United States Patent [19]
Ondetti

[11] Patent Number: 4,611,002
[45] Date of Patent: Sep. 9, 1986

[54] CARBOXYMETHYL ESTERS OF MERCAPTOPROPANOIC ACIDS AS ENKEPHALINASE INHIBITORS

[75] Inventor: Miguel A. Ondetti, Princeton, N.J.

[73] Assignee: E. R. Squibb and Sons, Inc., Princeton, N.J.

[21] Appl. No.: 618,720

[22] Filed: Jun. 8, 1984

Related U.S. Application Data

[63] Continuation-in-part of Ser. No. 815,472, Jul. 14, 1977, abandoned.

[51] Int. Cl.$^4$ ............... A61K 31/22; A61K 31/21; A61K 31/265; A61K 31/405
[52] U.S. Cl. .................. 514/419; 514/513; 514/533; 514/547; 548/494; 560/15; 560/147; 558/240
[58] Field of Search ........... 548/494; 560/147, 15; 260/455 R; 514/419, 513, 532, 550, 533, 547

[56] References Cited

U.S. PATENT DOCUMENTS 4,053,651 10/1977 Ondetti et al. .
4,235,885 11/1980 Sundeen et al. .
4,242,265 12/1980 Wade et al. .............. 548/341
4,297,275 11/1981 Sundeen et al. .
4,327,111 4/1982 Sundeen et al. .
4,401,677 8/1983 Greenberg et al. .
4,513,009 4/1985 Roques et al. .............. 514/513
4,567,198 1/1986 Delevalleé et al. .............. 514/513

FOREIGN PATENT DOCUMENTS 38758 4/1981 European Pat. Off. .
54882 12/1981 European Pat. Off. .
2556721 6/1985 France .............. 514/513

OTHER PUBLICATIONS

Roques et al., (Nature), vol. 288, Nov. 1980, pp. 286–288.
Roques et al., (Proc. Natl. Acad. Sci.) (USA), vol. 80, 1983, pp. 3178–3182.
Mumford et al., (Biochemical and Biophysical Res. Comm.), vol. 109, No. 4, 1982, pp. 1303–1309.
Cushman et al., (Biochemistry), vol. 16, No. 25, 1977, pp. 5484–5491.
Burger, Medicinal Chemistry, (Second Edition, New York, 1960), pp. 77–78.

Primary Examiner—Alton D. Rollins
Attorney, Agent, or Firm—Lawrence S. Levinson; Burton Rodney

[57] ABSTRACT

New carboxymethyl esters of mercaptopropanoic acids, and salts thereof, have the formula

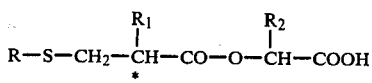

wherein
R is hydrogen or lower alkanoyl;
$R_1$ is hydrogen, lower alkyl, phenylalkyl and phenyl;
$R_2$ is hydrogen, lower alkyl, phenyl, phenyl-lower alkyl, 4-hydroxyphenyl-lower alkyl or indolyl-lower alkyl.

These compounds are useful as enkephalinase inhibitors and hypotensive agents.

5 Claims, No Drawings

CARBOXYMETHYL ESTERS OF MERCAPTOPROPANOIC ACIDS AS ENKEPHALINASE INHIBITORS

REFERENCE TO OTHER APPLICATIONS

This application is a continuation-in-part of U.S. patent application Ser. No. 815,472, filed July 14, 1977, abandoned.

RELATED APPLICATIONS

U.S. patent application Ser. No. 538,731, filed Oct. 3, 1983, now abandoned, discloses enkephalinase inhibitors having the structural formula

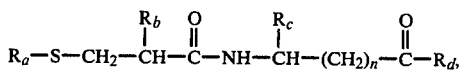

wherein $R_a$ is hydrogen or specified acyl groups, $R_b$ is alkyl, arylalkyl, or specified (heteroaryl)alkyl groups, $R_c$ is hydrogen, alkyl, aryl, arylalkyl, or specified (heteroaryl)alkyl groups, $R_d$ is hydroxy, alkoxy, amino or specified substituted amino groups, and n is an integer of 1 to 8.

U.S. patent application Ser. No. 595,765, filed Apr. 2, 1984, discloses compounds having the formula

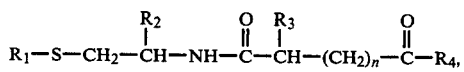

and pharmaceutically acceptable salts thereof, are useful analgesic agents. In formula I, and throughout the specification, the symbols are as defined below.

$R_1$ is hydrogen or

wherein $R_5$ is alkyl, aryl, arylalkyl, heteroaryl, or (heteroaryl)alkyl;

$R_2$ and $R_3$ are each independently hydrogen, alkyl, (cycloalkyl)alkyl, aryl, arylalkyl, heteroaryl, or (heteroaryl)alkyl;

$R_4$ is hydroxy, alkoxy, arylalkoxy, (heteroaryl)alkoxy, (substituted alkyl)oxy, or $-NR_6R_7$, wherein $R_6$ and $R_7$ are each independently hydrogen, alkyl, substituted alkyl, aryl, arylalkyl, or (heteroaryl)alkyl; and n is an integer of 1 to 15.

BACKGROUND OF THE INVENTION

Greenberg et al. in U.S. Pat. No. 4,401,677 disclose that various mercaptoalkanoyl α-amino acids are useful analgesic agents due to their enkephalinase inhibition activity.

Ondetti et al. in U.S. Pat. No. 4,053,651 disclose that various mercaptoalkanoyl and acylmercaptoalkanoyl α-aminoacids are useful hypotensive agents due to their angiotensin converting enzyme inhibition activity.

Roques et al. (Nature, Vol. 288, November 1980, p. 286–288) disclose that thiorphan, [(D,L)-3-mercapto-2-benzylpropanoyl]glycine, is an inhibitor of enkephalinase in vitro in nanomolar concentrations and in vivo after either intracerebroventricular or systemic administration.

Roques et al. (Proc. Natl. Acad. Sci. (U.S.A.) Vol. 80, 1983, p. 3178–3182) disclose thiorphan and its retro-inverso isomer, and their activity as inhibitors of enkephalinase.

Roques et al. in European patent application No. 38,758 disclose various α-amino acid derivatives including mercaptoalkanoyl and acylmercaptoalkanoyl derivatives as possessing enkephalinase inhibition activity.

Mumford et al. (Biochemical and Biophysical Research Comm., Vol. 109, No. 4, 1982, p. 1303–1309) disclose that various substituted N-carboxymethyl dipeptides including those having a terminal β-alanine group possess enkephalinase inhibition activity.

Berger et al. in European patent application No. 54,862 disclose enkephalinase inhibiting peptides having the structural formula

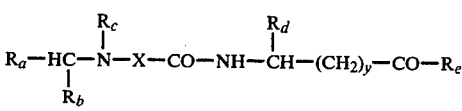

wherein $R_b$ is a carboxylic or phosphonic acid or ester and y is 0, 1, 2 or 3.

Cushman et al. (Biochemistry, Vol. 16, No. 25, 1977, p. 5484–5491) disclose various carboxyalkanoyl and mercaptoalkanoyl amino acids as angiotensin converting enzyme inhibitors. Among the compounds disclosed is

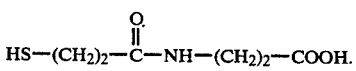

Sundeen et al. in U.S. Pat. Nos. 4,235,885 and 4,297,275 disclose mammalian collagenase inhibitors including mercaptoalkanoyl and acylmercaptoalkanoyl compounds having the structural formula

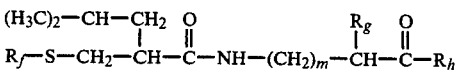

wherein m is zero or an integer from 1 to 9, $R_g$ can be, inter alia, hydrogen and $R_h$ can be inter alia, hydroxy and amino.

Sundeen et al. in U.S. Pat. No. 4,327,111 disclose mammalian collagenase inhibitors including mercaptoalkanoyl and acylmercaptoalkanoyl compounds of the formula

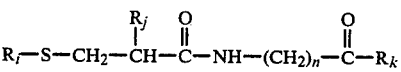

wherein $R_k$ is hydrogen, alkyl or aryl, n is an integer from 1 to 20, and $R_j$ is alkyl of 3 to 8 carbons, cycloalkyl of 3 to 7 carbons, aryl, or arylalkyl.

DETAILED DESCRIPTION OF THE INVENTION

This invention relates to new carboxymethyl esters of mercaptopropanoic acids which have the formula

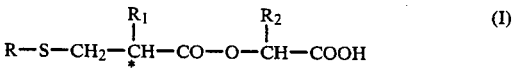

and to salts thereof.

In formula I and throughout this specification, the symbols have the meanings described below.

R is hydrogen or lower alkanoyl.

$R_1$ is hydrogen, lower alkyl, phenylalkyl and phenyl.

$R_2$ is hydrogen, lower alkyl, phenyl, phenyl-lower alkyl, 4-hydroxyphenyl-lower alkyl or indolyl-lower alkyl.

The lower alkyl groups are straight or branched chain hydrocarbon radicals having up to seven carbon atoms, e.g., methyl, ethyl, propyl, isopropyl, butyl, sec-butyl and the like. The $C_1$-$C_4$ and especially $C_2$-$C_2$ alkyl groups are preferred. The phenyl-lower alkyl and indolyl-lower alkyl groups include lower alkyl groups of the same type (with the same preferences expressed above.)

The lower alkanoyl groups are the acyl radicals of the lower ($C_2$-$C_7$) fatty acids, e.g., acetyl, propionyl, butyryl, isobutyryl and the like. The members mentioned, and especially acetyl, are preferred.

Preferred members of the invention are those compounds of formula I wherein R is hydrogen or lower alkanoyl, especially acetyl; $R_1$ is phenyl-lower alkyl, especially benzyl; and $R_2$ is hydrogen, phenyl-lower alkyl or indolyl lower alkyl especially phenylmethyl.

The compounds of formula I are produced by acylation of an α-hydroxy acid having the formula

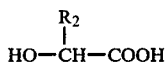

(II)

with an acid having the formula

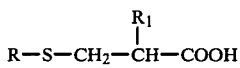

(III)

by conventional esterification procedures.

A preferred method comprises activating the acid of formula III with carbodiimidazole to form the acylimidazole intermediate having the formula

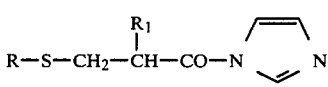

(IV)

which is used without isolation. It is also preferred to form a product wherein R is lower alkanoyl, then treat the acyl derivative with ammonia or concentrated ammonium hydroxide to obtain the product wherein R is hydrogen.

The carbon atoms marked with an asterisk in formula I are asymmetric if $R_1$ and $R_2$ are other than hydrogen. Thus, the compounds with the asymmetric carbon exist as diastereoisomers or in racemic mixtures thereof. All of these are within the scope of the invention.

The α-hydroxy acids of formula II are well known in the literature and can be produced by the many methods available.

The mercaptopropanoic acids of formula III can be produced as described in the U.S. Pat. Nos. 4,053,651 and 4,105,776, e.g., by reacting a thioacid of the formula

 (VI)

wherein $R_4$ is lower alkyl, with an acrylic acid having the formula

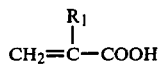

(VII)

The $R_4$—CO group can be removed at this stage or later by treatment with ammonia or concentrated ammonium hydroxide as described above.

The compounds of formula I form the common (basic) salts of carboxylic acid, e.g., by reaction with inorganic or organic bases. Such salts include ammonium salts, alkali metal salts like sodium and potassium salts, alkaline earth metal salts like calcium and magnesium salts, salts with organic bases, e.g., dicyclohexylamine, benzathine, hydrabamine and N-methyl-D-glucamine salts. Since some of the compounds of formula I are not readily obtainable as crystalline substances with well defined melting points, the salts (which are not necessarily physiologically acceptable) provide means to isolate and characterize the product.

Additional experimental details can be found in the illustrative examples below.

The compounds of this invention can be administered to a mammalian specie as an analgesic agent due to their ability to inhibit enkephalinase activity. While not limiting the scope of the invention to a specific theory or mechanism of action, it has been suggested that the endogenous opioid pentapeptides, [Met[5]]-enkephalin(Try-Gly-Gly-Phe-Met) and [Leu[5]]-enkephalin(Tyr-Gly-Gly-Phe-Leu), are neurotransmitters involved in central pain mediation (Hughes et al., Nature, Vol. 258, December 1975, p. 577–579) and that these endogenous opioid peptides are functionally inactivated by cleavage of their Gly[3]-Phe[4] peptide bonds by a specific peptidase, enkephalinase presumed to be specifically located at nerve terminals in the brain where enkephalins are released (Malfroy et al., Nature, Vol. 276, November 1978, p. 523–526). Specific inhibitors of this enkephalinase enhance the recovery of endogenous enkephalins released from isolated brain slices (Patey et al., Science, Vol. 212, June 1981, p. 1153–1155) and cause analgesia in mice that is reversed by the opioid antagonist naloxone (Roques et al., supra). In addition to analgesia, other pharmaceutical actions such as antitussive or antidiarrheal activities may result from prolonging the action of the body's natural opiates released from peripheral as well as central sites.

By the administration of a composition containing one or a combination of compounds of this invention, pain is alleviated in the mammalian host. A single dose, or preferably two to four divided daily doses, provided on a basis of about 0.1 to about 100 mg per kilogram of body weight per day, preferably about 1 to about 50 mg per kilogram per day, produces the desired analgesic activity. The composition is preferably administered orally but parenteral routes such as subcutaneous can also be employed.

In particular, the compounds of formula I, possess enkephalinase inhibition activity, and are far more active in this regard than prior art corresponding α-amino acid converting enzyme inhibitors. Administration of the compounds of formula I will produce a selective analgesic effect not possible with the α-amino acid compounds of the prior art.

The compounds of this invention can also be formulated in combination with an aminopeptidase inhibitor for the treatment of pain in mammalian species. Aminopeptidase inhibitors are known in the art; see, for example, Wagner et al., *Journal of Neurochemistry*, Vol. 37, p. 709–713 (1981).

The compounds of formula I, and the pharmaceutically acceptable salts thereof, are also hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglubulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus, by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg, preferably about 1 to 50 mg per kg of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure or in alleviating pain in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and represent preferred embodiments. All temperatures are in degrees Celsius.

EXAMPLE 1

O-(3-Acetylthiopropanoyl)glycolic Acid 3-(Acetylthio)propanoic acid (2.96 g) and 1,1'-carboxyldiimidazole (3.24 g) are dissolved in 20 ml of dry tetrahydrofuran with stirring at room temperature. After twenty minutes, a solution of glycolic acid (1.52 g) and 2.80 ml of triethylamine in 15 ml of dry tetrahydrofuran are added. The reaction mixture is stored overnight at room temperature. The tetrahydrofuran is removed in vacuo, the crude residue taken up into ethyl acetate, washed with 1N hydrochloric acid and three times with water, dried over magnesium sulfate and the O-(3-acetylthiopropanoyl)glycolic acid is concentrated to dryness in vacuo, yield 3.9 g. This is dissolved in ether and dicyclohexylamine is added. The dicyclohexylamine salt precipitates, yield 2.85 g.; m.p. 150–157°. The salt is converted to the free acid by adding to ethyl acetate and adding 10% potassium bisulfate solution, yield 1.5 g.

EXAMPLE 2

O-(3-Mercaptopropanoyl)glycolic Acid

O-(3-acetylthiopropanoyl)glycolic acid from Example 1 (1.3 g), under a blanket of argon is treated for fifteen minutes with a cold solution of 7 ml of water and 7 ml of concentrated ammonium hydroxide. This is chilled, acidified with concentrated hydrochloric acid and extracted into ethyl acetate, yield: 1.2 g. This product O-(3-mercaptopropanoyl)glycolic acid is chromatographed on DEAE Sephadex A25 (Polidextrane anion exchange resin) with a linear gradient of ammonium bicarbonate. The desired fractions (45–70; U.V. peak at 254 nm.) are pooled, concentrated and lyophilized. This ammonium salt of O-(3-mercaptopropanoyl)glycolic acid is converted to the free acid by treatment with Dowex 50WX2 cation exchange resin, yield 320 mg. The O-(3-mercaptopropanoyl)glycolic acid is converted to the dicyclohexylamine salt by dissolving in ether and precipitating by the addition of dicyclohexylamine, m.p. 143°–144°.

EXAMPLE 3

O-[3-(Acetylthio)-2-methylpropanoyl]glycolic Acid

A mixture of thioacetic acid (50 g) and methacrylic acid (40.7 g) is heated on the steam bath for one hour and then stored at room temperature for 18 hours. After confirming by nmr spectroscopy that complete reaction of the methacrylic acid has been achieved, the reaction mixture is distilled in vacuo and the desired 3-acetylthio-2-methylpropanoic acid is separated in the fraction with boiling point 128.5°–131° (2.6 mmHg.), yield 64 g.

3-Acetylthio-2-methylpropanoic acid (6.48 g) is taken into 40 ml of dry tetrahydrofuran. To this 1,1'-carbonyldiimidazole (0.48 g) is added and stirred for 30 minutes at room temperature. Glycolic acid (6.08 g) and 11.2 ml of triethylamine in 60 ml of dry tetrahydrofuran are added. After several minutes, the imidazole salt of glycolic acid begins to come out of solution. The reaction is permitted to run overnight at room temperature. The crystalline salt is filtered and the filtrate concentrated to dryness in vacuo. The residue is taken up into ethyl acetate, washed with 1N hydrochloric acid and three times with water, dried over magnesium sulfate and concentrated to dryness in vacuo. This product is converted to its dicyclohexylamine salt by dissolving in ether/hexane and precipitating by the addition of dicyclohexylamine. The salt is recrystallized from ether, m.p. 120°–122°. This salt is then converted to the free acid, O-[3-(acetylthio)-2-methylpropanoyl]glycolic acid by adding to ethyl acetate, adding 10% potassium bisulfate solution, then crystallizing from ethyl/hexane, yield 2.96 g., m.p. 50°–51°.

EXAMPLE 4

O-DL-(3-Mercapto-2-methylpropanoyl)glycolic Acid

O-[3-(Acetylthio)-2-methylpropanoyl]glycolic acid (1.5 g) is placed under a blanket of argon. To this a cold solution of 7.5 ml of concentrated ammonium hydroxide and 7.5 ml of water is added and the mixture is stored for 15 minutes at room temperature. This is then acidified with concentrated hydrochloric acid and extracted with ethyl acetate, yield 1.3 g. This product is dissolved in ether/hexane and dicyclohexylamine is added to precipitate the dicyclohexylamine salt, yield 2.24 g., m.p. 96°–98°. A 1.9 g aliquot of the salt is converted to the free O-DL-(3-mercapto-2-methylpropanoyl)glycolic acid by adding to ethyl acetate and adding 10% potassium bisulfate solution, yield 0.9 g. The product is a heavy oil which is chromatographed on silica gel (benzene 7:2 acetic acid), $R_f=0.49$, traces $R_f=0.32$ and 0.57.

EXAMPLE 5

O-L-[3-(Acetylthio)propanoyl]-3-phenyllactic Acid 3-(Acetylthio)propanoic acid (1.48 g) is added to 10 ml of dry tetrahydrofuran with stirring. To this 1,1'-carbonyldiimidazole (1.62 g) is added and the mixture stirred for twenty minutes at room temperature. L-(−)-3-phenyllactic acid (1.66 g) is added in a solution of 7.5 ml of dry tetrahydrofuran and 1.4 ml of triethylamine. The reaction mixture is stored overnight at room temperature. The tetrahydrofuran is removed in vacuo, the residue is taken up into ethyl acetate, washed with 1N hydrochloric acid, three times with water, dried over magnesium sulfate and concentrated to dryness in vacuo, yield 2.8 g. The O-L-[3-(acetylthio)propanoyl]-3-phenyllactic acid is purified on a silica gel column, eluting with benzene 7:1 acetic acid, yield 1.7 g.

EXAMPLE 6

O-L-(3-Mercaptopropanoyl)-3-phenyllactic Acid

To 1.5 g of O-L-[3-(acetylthio)propanoyl]3-phenyllactic acid a solution of 7.5 ml of water and 7.5 ml of concentrated ammonium hydroxide is added under an argon blanket. After fifteen minutes, the reaction mixture is chilled, acidified with concentrated hydrochloric acid and extracted into ethyl acetate, yield 1.1 g. The product, O-L-(3-mercaptopropanoyl)-3-phenyllactic acid is purified on a silica gel column, eluting with benzene 14:1 acetic acid, yield 357 mg. A small portion of the semi-solid product is converted to its dicyclohexylamine salt by dissolving in ether/hexane and precipitating with dicyclohexylamine, m.p. 100°.

EXAMPLE 7

O-DL-(3-Acetylthiopropanoyl)-3-indolelactic Acid

By substituting DL-3-indolelactic acid for the L-β-phenyllactic acid in the procedure of Example 5, O-DL-(3-acetylthiopropanoyl)-3-indolelactic acid is obtained.

EXAMPLE 8

O-DL-(3-Mercaptopropanoyl)-3-indolelactic Acid

By substituting O-DL-(3-acetylthiopropanoyl)-3-indolelactic acid for the O-L-(3-acetylthiopropanoyl)-3-phenyllactic acid in the procedure of Example 6, O-DL-(3-mercaptopropanoyl)-3-indolelactic acid is obtained.

EXAMPLE 9

O-DL-(3-Mercapto-2-methylpropanoyl)-3-indolelactic acid

By substituting 3-indolelactic acid for the glycolic acid in the procedure of Example 3 and then submitting the product to the procedure of Example 4, O-DL-[3-(acetylthio)-2-methylpropanoyl]-3-indolelactic acid and O-DL-(3-mercapto-2-methylpropanoyl)-3-indolelactic acid are obtained.

EXAMPLE 10

O-L-(3-Mercaptopropanoyl)lactic Acid

By substituting L-lactic acid for the glycolic acid in the procedure of Example 1 and then submitting the product to the procedure of Example 2, O-L-(3-acetylthiopropanoyl)lactic acid and O-L-(3-mercaptopropanoyl)lactic acid are obtained.

EXAMPLE 11

O-L-(3-Mercaptopropanoyl)-α-hydroxyisocaproic acid

By substituting L-α-hydroxyisocaproic acid [Winitz, et al., J. Am. Chem. Soc. 78, 2423 (1956)] for the glycolic acid in the procedure of Example 1 and then submitting the product to the procedure of Example 2, O-L-(3-acetylthiopropanoyl)-α-hydroxyisocaproic acid and O-L-(3-mercaptopropanoyl)-α-ahydroxyisocaproic acid are obtained.

EXAMPLE 12

O-L-(3-Acetylthiopropanoyl)-3-(p-tert-butoxyphenyl)-lactic acid

By substituting 3-(p-tert-butoxyphenyl)lactic acid [obtained from O-tert-butyl-L-tyrosine by the procedure described by H. D. Dakin and H. W. Dudley in J. Biol. Chem., 18, 29 (1914) for the preparation of 3-L-phenyllactic acid] for the 3-L-phenyllactic acid in the procedure of Example 5, O-L-(3-acetylthiopropanoyl)-3-(p-tert-butoxyphenyl)lactic acid is obtained.

EXAMPLE 13

O-L-(3-Mercaptopropanoyl)-3-p-hydroxyphenyllactic Acid

O-L-(3-acetylthiopropanoyl)-3-(p-tertbutoxyphenyl)-lactic acid (1.8 g) is dissolved in trifluoroacetic acid (15 ml) and the solution is stored at room temperature for one hour. After removing the trifluoroacetic acid in vacuo, the residue is dissolved in a mixture of water (7.5 ml) and concentrated ammonium hydroxide (7.5 ml) under an argon blanket. After fifteen minutes, the reaction mixture is chilled, acidified with concentrated hydrochloric acid and extracted with ethyl acetate. The organic layer is concentrated in vacuo to yield O-L-(3-mercaptopropanoyl)-3-phydroxyphenyllactic acid.

EXAMPLE 14

O-(3-Mercaptopropanoyl)mandelic Acid

By substituting mandelic acid for the L-3-phenyllactic acid in the procedure of Example 5, and then submitting the product to the procedure of Example 6, O-(3-acetylthiopropanoyl)mandelic acid and O-(3-mercaptopropanoyl)mandelic acid are obtained.

EXAMPLE 15

O-(α-Benzyl-β-mercaptopropanoyl)glycolic acid

By substituting 3-(acetylthio)-2-benzylpropanoic acid for 3-(acetylthio)propanoic acid in the procedure of Example 1 and then submitting the product to the procedure of Example 2, [(3-acetylthio)- 2-benzylpropanoyl]glycolic acid and the title compound are obtained.

EXAMPLE 16

O-(α-Phenyl-β-mercaptopropanoyl)glycolic acid

By substituting 3-(acetylthio)-2-phenyl propanoic acid for 3-(acetylthio)propanoic acid in the procedure of Example 1 and then submitting the product to the procedure of Example 2, [3-(acetylthio)-2-phenylpropanoyl]glycolic acid and the title compound are obtained.

EXAMPLE 17

O-L-(α-Benzyl-β-mercaptopropanoyl)-3-phenyllactic acid

By substituting 3-(acetylthio)-2-benzylpropanoic acid for 3-(acetylthio)propanoic acid in the procedure of Example 5 and then submitting the product to the procedure of Example 6, O-L-[3-(acetylthio)-2-phenylpropanoyl]-3-phenyllactic acid and the title compound are obtained.

EXAMPLE 18

O-(α-Phenyl-β-mercaptopropanoyl)mandelic acid

By substituting 3-(acetylthio)-2-phenylpropanoic acid for 3-(acetylthio)propanoic acid and mandelic acid for L-3-phenyllactic acid in the procedure of Example 5 and then submitting the product to the procedure of Example 6, O-[3-(acetylthio)-2-phenylpropanoyl]mandelic acid and the title compound is obtained.

EXAMPLE 19

O-DL-(α-Benzyl-β-mercaptopropanoyl)-3-indolelactic acid

By substituting 3-(aoetylthio)-2-benzylpropanoic acid for 3-acetylthio-2-methylpropanoic acid and 3-indolelactic acid for the glycolic acid in the procedure of Example 3 and then submitting the product to the procedure of Example 4, O-DL-[3-(acetylthio)-2-benzylpropanoyl]-3-indolelactic acid and the title compound are obtained.

EXAMPLE 20

O-DL-(α-Phenyl-β-mercaptopropanoyl)lactic acid

By substituting 3-(acetylthio)-2-phenylpropanoic acid for 3-(acetylthio)propanoic acid and DL-lactic acid for the glycolic acid in the procedure of Example 1 and then submitting the product to the procedure of Example 2, O-DL-[3-(acetylthio)-2-phenylpropanoyl]-lactic acid and the title compound are obtained.

EXAMPLE 21

O-L-(α-Benzyl-β-mercaptopropanoyl)-α-hydroxyisocaproic acid

By substituting 3-(acetylthio)-2-benzylpropanoic acid for 3-(acetylthio)propanoic acid and L-α-hydroxyisocaproic acid for the glycolic acid in the procedure of Example 1 and then submitting the product to the procedure of Example 2, O-L-[3-(acetylthio)-2-benzylpropanoyl]-α-hydroxyisocaproic acid and the title compound are obtained.

What is claimed is:

1. A method of relieving pain in a mammalian species, which comprises administering to said mammalian species a composition containing an analgesically effective amount of a compound of the formula

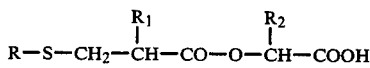

wherein

R is hydrogen or lower alkanoyl;

$R_1$ is hydrogen, alkyl, phenyl-lower alkyl or phenyl;

$R_2$ is hydrogen, lower alkyl, phenyl, phenyl-lower alkyl, 4-hydroxyphenyl-lower alkyl or indolyl-3-lower alkyl; and salts thereof.

2. The method as defined in claim 1 wherein $R_1$ is phenyl-lower alkyl or phenyl.

3. The method as defined in claim 1 wherein $R_1$ is benzyl.

4. The method as defined in claim 1 wherein R is hydrogen, $R_2$ is hydrogen, and $R_1$ is benzyl or phenyl.

5. The method as defined in claim 4 wherein $R_1$ is benzyl.

* * * * *

UNITED STATES PATENT AND TRADEMARK OFFICE
CERTIFICATE OF CORRECTION

PATENT NO. : 4,611,002
DATED : September 9, 1986
INVENTOR(S) : Miguel A. Ondetti It is certified that error appears in the above-identified patent and that said Letters Patent is hereby corrected as shown below:

Column 3, line 11, "$C_2$-$C_2$" should read --$C_1$-$C_2$--.

Signed and Sealed this

Sixteenth Day of December, 1986

Attest:

DONALD J. QUIGG

Attesting Officer

Commissioner of Patents and Trademarks